United States Patent [19]

Lin et al.

[11] Patent Number: 5,199,297

[45] Date of Patent: Apr. 6, 1993

[54] THIN WALLED CAN TEMPERATURE AND PRESSURE MONITORING DEVICE AND METHOD

[75] Inventors: Ellen Y. Lin; Timothy T. Raw, both of St. Louis, Mo.

[73] Assignee: Anheuser-Busch, Incorporated, St. Louis, Mo.

[21] Appl. No.: 771,622

[22] Filed: Oct. 4, 1991

[51] Int. Cl.⁵ ............................................. G01N 33/14
[52] U.S. Cl. ..................................... 73/52; 73/863.85; 374/143; 374/155
[58] Field of Search ...................... 73/52, 49.3, 863.85, 73/866.5, 756; 374/143, 155

[56] References Cited

U.S. PATENT DOCUMENTS

| | | | |
|---|---|---|---|
| 900,324 | 10/1908 | Swangren | 73/49.3 |
| 3,374,678 | 3/1968 | McGuckin | 73/863.85 |
| 4,788,871 | 12/1988 | Nelson et al. | 374/143 X |
| 4,934,200 | 6/1990 | Lantz | 73/863.85 |

Primary Examiner—Hezron E. Williams
Assistant Examiner—Joseph W. Roskos
Attorney, Agent, or Firm—Polster, Lieder, Woodruff & Lucchesi

[57] ABSTRACT

A can testing device for measuring pressure and temperature in a sealed container wherein a strap encircles the body of the container circumferentially and a probe affixed to the strap penetrates the sidewall of the container to allow instruments for measuring the temperature and pressure of the container contents to come into physical contact with said contents.

17 Claims, 1 Drawing Sheet

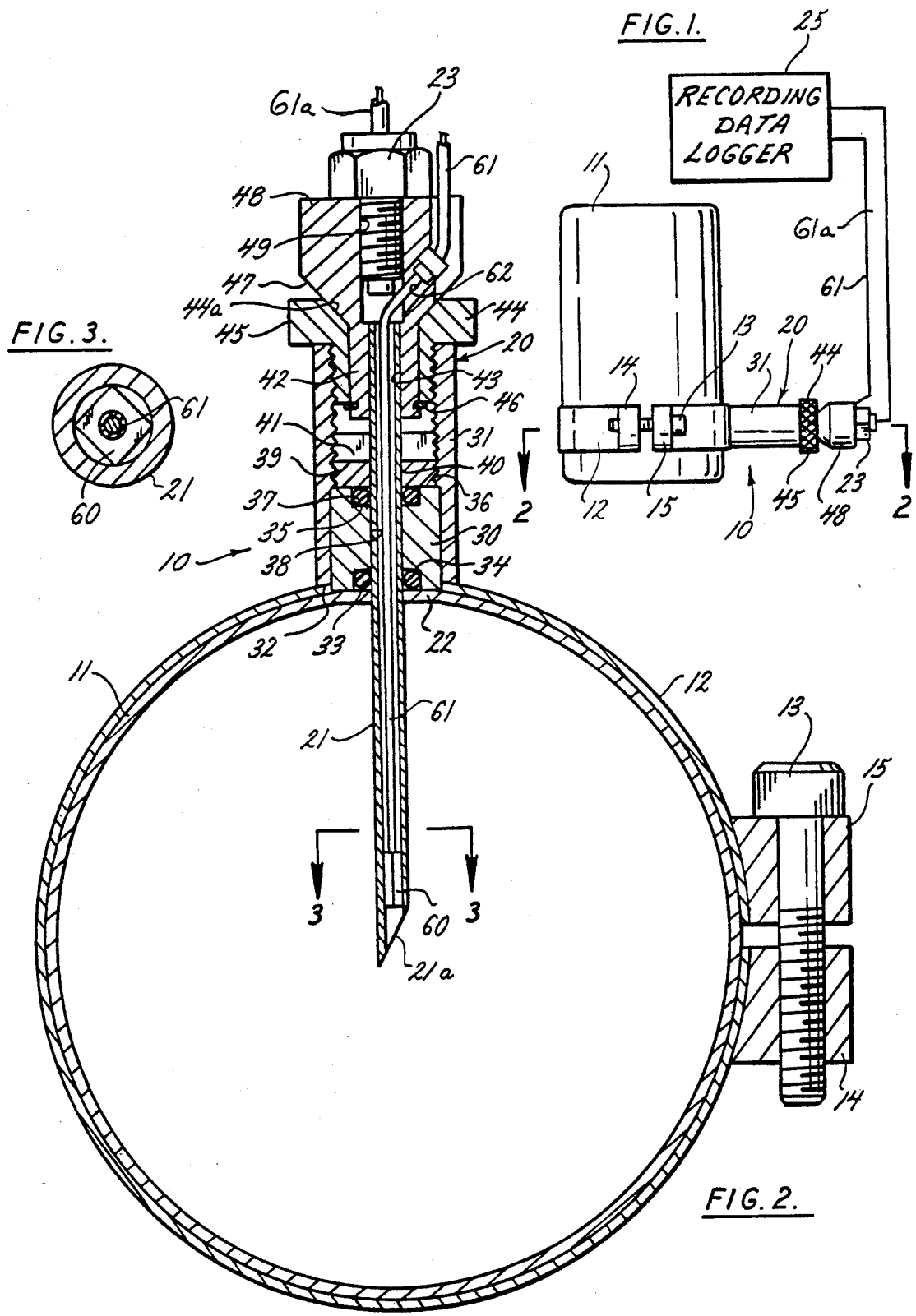

THIN WALLED CAN TEMPERATURE AND PRESSURE MONITORING DEVICE AND METHOD

BACKGROUND OF THE INVENTION

This application relates to the art of monitoring the temperature and pressure inside a can of carbonated beverage, particularly a can of beer. Specifically, this invention relates to a probe and clamp assembly that is utilized with a battery powered data acquisition system to monitor the pressure and temperature of beer cans, especially during the beer pasteurization process.

This assembly is used to study the effects of process variables, such as $CO_2$, temperature, fill, and pasteurizer operating conditions on can internal pressure development, information which enables the use of lighter containers by optimizing the operating conditions to reduce internal pressure.

To save metals in aluminum cans and lids, the current trend in can and lid making is to make the walls of the cans and the lids thinner and thinner. As the can walls become thinner, it is more important that can and beverage manufacturers have a way of measuring the pressure within the can to ensure lids and cans will not buckle and reverse during pasteurization or kept in the trunk of a car in the hot summer.

There are commercial devices which are designed for this purpose and there also are a number of devices shown in the patent art for this purpose. However, current devices tend to puncture the top or bottom of the can, and press the ends tightly. This will not allow the ends to grow, caused by high internal pressure developed during pasteurization. The can ends are subjected to unusual stress and may even be deformed. The side walls of present cans are so thin that they are subject to being easily deformed by any unusual stress.

Among the prior art devices known are Cochran U.S. Pat. No. 1,539,937 and Hoff U.S. Pat. No. 1,211,942. These patents show devices which pierce the cap of a bottle and are designed to engage the throat of a bottle while piercing the top wall of the cap. Elert U.S. Pat. No. 4,555,935 is designed to test an empty can to determine if the can meets specifications.

Doudera U.S. Pat. No. 2,737,803 and U.S. Pat. No. 2,749,744 are designed to pierce the top wall of a container. Benjamin U.S. Pat. No. 2,036,618 is a device for piercing the top wall of a container with a probe to measure the temperature thereof. Fredricksen U.S. Pat. No. 1,918,258 shows a combination pressure and temperature measuring device designed to pierce the top of a bottle cap. Neuman U.S. Pat. No. 2,457,707 is designed to sample the gas content of a container by engaging the side wall of the container and piercing the container through the top wall.

Werner U.S. Pat. No. 983,962 involves a U-shaped device with opposed arcuate segments designed to engage portions of a can side wall so that one side can be punctured. The device is designed to pressurize the can so that the soldered seams of the empty can may be tested for tightness. The hole then is designed to be filled with solder so the can may be filled and used.

Bellgardt U.S. Pat. No. 4,569,228 shows a probe which can be inserted into a container for measuring the pressure and temperature of the material in the container. Nelson U.S. Pat. Nos. 4,739,699 and 4,788,871 are designed to measure temperature and pressure in a plastic container.

Other patents known to us include U.S. Pat. Nos. 1,344,515, 2,393,552, 2,512,134, 3,958,448, 4,718,776, 4,733,555 and 4,926,681.

The present invention is placed in a receptacle with a battery operated temperature and pressure sensing device which records temperature and pressure as a function of time. The probe is inserted into the container at the thicker wall of the container so as to reside at the cold spot in the can and the temperature and pressure in the can is recorded through the run. The device monitors process time, pasteurizer zone temperatures, can internal pressure, and calculates pasteurization units (P.U.), $CO_2$ volume, and beer out temperature at the end of pasteurization. This information is used to determine optium operating conditions for the pasteurizer.

The principal object of the present invention is to provide a device for measuring the temperature and pressure in filled thin wall containers of carbonated beverages. It is another main object of this invention to provide a device for measuring the temperature and pressure in a beverage can which includes a thin band for encircling a circular segment of the side wall of the can to prevent distortion of said wall and at the same time having a hollow needle adapted to penetrate the container wall with internal seal means to prevent loss of container fluid or pressure, and consequent false readings, and secondary seal means to seal the device to the container outer wall.

The sealing system in the clamp allows the probe to be inserted into the container with no liquid or pressure loss. The clamp seals against the sidewall of the can without deforming the container. An internal seal in the clamping device seals against the outside diameter of the probe.

The clamp allows precise positioning of the temperature probe at the coldspot of the container, approximately 0.25 inch above the bottom of the center of the can.

The small mass and volume of the probe minimize the heat effect and provides a fast response to temperature changes in the beer from pasteurizer spray water.

When in use, the clamp is assembled onto the exterior of the can; the probe is inserted into the clamp; the probe penetrates the can and remains in the beer until the monitoring is complete; and then is removed by a technician.

These and other objects and advantages of the present invention will become apparent hereinafter.

SUMMARY OF THE INVENTION

The present invention comprises a device for measuring the internal temperature and pressure of a thin walled can by piercing the side wall of the can while supporting the can side wall circumferentially in the plane where the can is pierced.

The invention also consists in the parts and in the arrangements and combinations of parts hereinafter described and claimed.

In the accompanying drawings which form part of the specification, like numerals and letters refer to like parts wherever they occur.

FIG. 1 is a schematic representation of this invention;

FIG. 2 is a sectional view taken along line 2—2 of FIG. 1; and

FIG. 3 is a sectional view taken along line 3—3 of FIG. 2.

DETAILED DESCRIPTION

In the pasteurization of beer or other canned or bottled products, typically a tunnel pasteurizer, the pressure inside a container develops up to 90 PSI.

With the thinner and thinner cans used for product, the internal pressure in a can is an important factor in pasteurization control. The present device incorporates both a temperature and a pressure sensor in one piece of equipment and measures the internal temperature at the cold spot and the direct internal pressure. A critical factor in obtaining direct internal temperature and pressure measurements is the sealing of the probe used to penetrate the can and the reinforcement of the thin walled can during piercing to prevent collapse or deformation of the can.

FIG. 1 shows the overall apparatus arrangement of this invention. The pressure and temperature tester 10 is shown attached to a can 11 adjacent to its bottom. The tester 10 has a band clamp 12 which fits entirely around the circumference of the can 11 and is fastened thereto by an attachment screw 13 which connects the free ends of the band 12. The screw 13 passes through threaded bosses 14 and 15 on the ends of the band 12. As the screw 13 is tightened, it brings the bosses 14 and 15 closer together to tighten the band 12 around the can 11.

The band 12 is attached to the tester body 20. Positioned within the tester body 20 is a probe 21 which is a hollow tube containing a temperature sensor. The probe 21 is adapted to be driven through the can body sidewall 22 to sample the contents of the can 11.

FIG. 2 shows the details of the can pressure and temperature tester 10. The clamp 12 is attached to the leading edge of a seal holder 30 which is secured in a cylindrical sleeve body 31. The holder 30 can be press fit, brazed or otherwise affixed to the sleeve 31 as desired. The seal holder 30 is illustrated as projecting beyond the working end 32 of the sleeve 31. It also projects beyond the clamp 12 so that it seats firmly against the can body side wall 22 and compresses an O-ring seal 33 into sealing engagement with the can body 22.

The seal holder 30 is provided with a seal retaining recess 34 in the leading edge into which the 0-ring 33 is positioned. A second recess 35 is located in the trailing end 36 of the holder 30 and a second 0-ring seal 37 is positioned therein. The recesses 34 and 35 surround a center throughbore 38 in the seal holder 30. The recess 34 in the leading face retains the 0-ring seal 30 which projects forwardly of the leading end of the seal holder 30 and is adapted to engage the outer surface of the can body 22 whose temperature and pressure is to be measured. The 0-ring 33 projects outwardly from the leading edge of the can tester 10 and is designed to be compressed against the outer surface of the can 11 in sealing engagement to prevent any gaseous pressure from escaping to atmosphere from the can 11 when it is pierced by the probe 21.

The recess 35 also retains an 0-ring seal 37 which is sized to seal against the probe 21 so as to further seal against loss of fluid from the can or loss of can internal pressure when the can is pierced by the probe 21.

A seal retainer 39 is threadedly engaged within the sleeve 31 and also is provided with a throughbore 40. The retainer 39 is adapted to be moved into engagement with the top face 36 of the seal holder 30 to retain the O-ring seal 37 around the probe 21. A slot 41 is provided in the top of the retainer 39 so that the retainer 39 can be turned into engagement with the seal holder 30.

A probe holder 42 is positioned in the sleeve body 31 and is provided with a throughbore 43 in which the probe 21 is positioned. The probe 21 is a hollow tube with a sharpened end 21a (FIG. 2) to pierce the can side wall. In some respects the probe 21 is similar to a hypodermic needle. The probe 21 is fixed to the holder 42 and moves therewith.

The holder 42 is slidably and rotatably positioned in a probe driver 44 which has a knurled or flattened shoulder 45 accessible to be grasped to rotate the driver 44. The driver 44 is engaged with the inside of the body 31 by a threaded engagement whereby rotation of the driver 44 moves it longitudinally with respect to the body 31. The holder 42 is retained by a snap ring lock fastener 46 in longitudinal engagement with the driver 44. The top surface 44 of the driver shoulder 44 abuts an external shoulder 47 on the head 48 of the holder 42 so that the holder 42 is longitudinally movable with the driver 44. Thus, rotation of the driver 44 will move the probe 21 into and out of engagement with the can body 11.

The free end of the holder head 45 is provided with a threaded socket 49 adapted to engage the transducer or pressure sensor 23.

FIGS. 2 also shows the temperature and pressure sensor aspect of the invention.

The probe 21 consists of a transducer 23 which measures the can pressure and a temperature sensor 60 which measures the temperature. The outputs from the pressure and temperature sensors are transmitted to a readout or recording data logger 25 where the pressure or temperature is displayed and/or recorded. This entire structure is passed through the pasteurizer during a commercial run.

The temperature sensing portion of the device includes the thermostat 60 connected by a lead 61 to a data logger 25. The lead 61 runs through the hollow probe 21 to an exit passage 62 in the head 48. A lead 61a also transmits pressure data to the logger 25.

The thermostat 60 is positioned by the probe 21 adjacent to the "cold sport" of the can. The probe 21 is sized to locate the thermostat 60 at the cold spot.

The critical part of this apparatus is the clamp 12 which encircles and supports the entire outer wall of the can being tested. This prevents distortion of the thin walled cans now being used. By measuring the pressure through the side wall to allow the ends to grow during pasteurization, false readings are avoided which can result when the top or bottom is punctured and the ends are pressed down.

This invention is intended to cover all changes and modifications of the example of the invention herein chosen for purposes of the disclosure which do not constitute departures from the spirit and scope of the invention.

What is claimed is:

1. A removable portable can testing device for measuring process variables in a filled sealed thin wall metallic can containing carbonated beverages comprising
   a) a body member,
   b) clamp means attached to the body member for removably engaging a complete circular segment of the outer periphery of a can body sidewall to support said can body against lateral pressure,
   c) a probe member longitudinally movable in the body member for engaging and piercing the can body to measure the variables within the sealed can body, d) means for sealing the can contents from being lost when the probe has pierced the can body, said seal means including a first seal for sealing against the outer surface of the metallic can body where the probe enters the can and second seal means for sealing around the probe, and e) means associated with the probe for measuring and reporting the numerical value of the variable being measured.

2. The can testing device of claim 1 wherein the clamp means includes straps having one end attached at the body member and free ends with adjustable tightening means positioned on said free ends and adapted to urge the free ends together to tighten the strap around the can body.

3. The device of claim 1 wherein the body member includes a housing, a seal holder having opposed recesses on opposed faces thereof positioned on the end of the housing and projecting beyond the end of the housing with the clamp means being attached to said seal holder, the first seal means being positioned in one of said recesses and projecting beyond the end face and adapted to seal against the can body, the second seal means being positioned in the opposed recess adapted to seal against the probe.

4. The device of claim 3 including a seal retainer having a throughbore which receives the probe and is in threaded engagement with the inner wall of the housing to compress the seal into sealing engagement with the probe.

5. The device of claim 4 including a probe holder movable through the housing and provided with means for connecting to the probe and to means for receiving and reporting the variable measured by the probe.

6. The device of claim 5 including a probe holder mover for reciprocating the probe longitudinally in the housing and driving the probe through the can wall into the can interior.

7. The device of claim 1 wherein the probe is hollow and is adapted to measure the pressure within the can.

8. The device of claim 1 wherein the probe is a temperature sensor designed to measure the temperature of the contents of the can.

9. The device of claim 7 including a temperature sensor positioned within the hollow probe adjacent to the cold spot of the can.

10. A can testing device for measuring process variables in a sealed can comprising a) a body member, said body member including a housing, a seal holder having opposed recesses on opposed faces thereof positioned on the end of the housing and projecting beyond the end of the housing, first and second seal means positioned in said recesses, the first seal being on the end adjacent to the strap means ad projecting beyond the end face and adapted to seal against the can body, the second seal being in the opposed recess adapted to seal against the probe, said seal means in combination preventing the can contents from being lost when the probe has pierced the can body, b) clamp means attached to the seal holder on said body member for engaging a circular segment of the outer periphery of a can body to support said can body against lateral pressure, c) a probe member longitudinally movable in the body member for engaging and piercing the can body to measure the variables within the sealed can body, and d) means associated with the probe for measuring and reporting the numerical value of the variable being measured.

11. The can testing device of claim 10 wherein the clamp means includes straps having one end attached at the body member and free ends with adjustable tightening means positioned on said free ends and adapted to urge the free ends together to tighten the strap around the can body.

12. The device of claim 10 including a seal retainer having a throughbore which receives the probe and being in threaded engagement with the inner wall of the housing to compress the second seal into engagement with the probe.

13. The device of claim 12 including a probe holder movable through the housing and provided with means for connecting to the probe and to means for receiving and reporting the variable measured by the probe.

14. The device of claim 13 including a probe holder mover for reciprocating the probe longitudinally in the housing and driving the probe through the can wall into the can interior.

15. The device of claim 14 wherein the probe is hollow and is adapted to measure the pressure within the can.

16. The device of claim 14 wherein the probe is a temperature sensor designed to measure the temperature of the contents of the can.

17. The device of claim 15 including a temperature sensor positioned within the hollow probe adjacent to the cold spot of the can.

* * * * *